(12) United States Patent
Holman et al.

(10) Patent No.: US 7,575,568 B2
(45) Date of Patent: Aug. 18, 2009

(54) CATHETER DISTAL TIP

(75) Inventors: Thomas J. Holman, Minneapolis, MN (US); Daniel K. Tomaschko, Savage, MN (US); Leo M. Klisch, Maple Grove, MN (US); Richard Olson, Blaine, MN (US); Joseph M Lyver, Hopkins, MN (US); Richard Dunn, Brooklyn Park, MN (US); David Griswold, Maple Grove, MN (US); Nie Tang, Maple Grove, MN (US); Lixiao Wang, Long Lake, MN (US)

(73) Assignee: Boston Scientific Scimed, Inc., Maple Grove, MN (US)

(*) Notice: Subject to any disclaimer, the term of this patent is extended or adjusted under 35 U.S.C. 154(b) by 325 days.

(21) Appl. No.: 10/732,983

(22) Filed: Dec. 10, 2003

(65) Prior Publication Data

US 2005/0131445 A1      Jun. 16, 2005

(51) Int. Cl.
*A61M 29/00* (2006.01)
(52) U.S. Cl. .................... 604/96.01; 606/194; 623/1.11
(58) Field of Classification Search ............ 604/103.06, 604/96.01, 102.02, 102.03, 103.07, 103.11, 604/103.12, 264, 523, 103, 103.09; 606/192, 606/194; 623/1.11
See application file for complete search history.

(56) References Cited

U.S. PATENT DOCUMENTS

| | | | | |
|---|---|---|---|---|
| 4,702,252 A * | 10/1987 | Brooks et al. | ............... | 606/195 |
| 4,896,669 A | 1/1990 | Bhate et al. | ................. | 606/194 |
| 4,921,483 A * | 5/1990 | Wijay et al. | .............. | 604/103.1 |
| 5,078,702 A | 1/1992 | Pomeranz | ................... | 604/280 |
| 5,240,537 A | 8/1993 | Bodicky | .................... | 156/244 |
| 5,270,086 A | 12/1993 | Hamlin | ...................... | 428/35.2 |
| 5,338,299 A * | 8/1994 | Barlow | .................. | 604/103.09 |
| 5,499,973 A | 3/1996 | Saab | ........................... | 604/96 |
| 5,538,513 A | 7/1996 | Okajima | .................... | 604/527 |
| 5,649,908 A * | 7/1997 | Itoh | ........................ | 604/96.01 |
| 5,683,347 A * | 11/1997 | Miyata et al. | ................. | 600/18 |
| 5,728,063 A | 3/1998 | Preissman et al. | ...... | 604/103.09 |
| 5,759,173 A | 6/1998 | Preissman et al. | ...... | 604/103.07 |
| 5,769,819 A * | 6/1998 | Schwab et al. | .............. | 604/103 |
| 5,769,830 A | 6/1998 | Parker | ........................ | 604/528 |
| 5,964,778 A | 10/1999 | Fugoso et al. | ................ | 606/194 |
| 6,010,521 A * | 1/2000 | Lee et al. | .................... | 606/194 |

(Continued)

FOREIGN PATENT DOCUMENTS

EP        0 742 029 A1      11/1996

(Continued)

OTHER PUBLICATIONS

U.S. Appl. No. 09/654,987, filed Sep. 5, 2000, Aiden Flanagan.

*Primary Examiner*—Nicholas D Lucchesi
*Assistant Examiner*—Christopher D Koharski
(74) *Attorney, Agent, or Firm*—Vidas, Arrett & Steinkraus, P.A.

(57) ABSTRACT

The present invention is directed to distal tip designs for catheter, wherein distal tip material is positioned about an inner shaft. The distal tip material may also be used as a tie layer for thermally bonding two incompatible materials together, such as a waist portion of a balloon to the inner shaft.

21 Claims, 18 Drawing Sheets

U.S. PATENT DOCUMENTS

| | | | | |
|---|---|---|---|---|
| 6,048,338 A * | 4/2000 | Larson et al. | | 604/523 |
| 6,165,166 A | 12/2000 | Samuelson et al. | | 604/524 |
| 6,171,295 B1 | 1/2001 | Garabedian et al. | | 604/524 |
| 6,171,297 B1 | 1/2001 | Pederson et al. | | |
| 6,187,130 B1 | 2/2001 | Berard et al. | | 156/294 |
| 6,193,738 B1 | 2/2001 | Tomaschko et al. | | 606/194 |
| 6,235,226 B1 | 5/2001 | Lee | | 264/130 |
| 6,319,228 B1 | 11/2001 | Kastenhofer | | 604/96.01 |
| 6,322,586 B1 | 11/2001 | Monroe et al. | | 623/1.11 |
| 6,368,301 B1 * | 4/2002 | Hamilton et al. | | 601/103 |
| 6,464,683 B1 | 10/2002 | Samuelson et al. | | 604/524 |
| 6,475,209 B1 * | 11/2002 | Larson et al. | | 604/525 |
| 6,530,938 B1 | 3/2003 | Lee et al. | | 606/194 |
| 6,575,934 B2 * | 6/2003 | Duchamp | | 604/102.02 |
| 6,652,507 B2 | 11/2003 | Pepin | | 604/523 |
| 6,746,424 B2 | 6/2004 | Stamberg | | 604/103.06 |
| 6,979,342 B2 * | 12/2005 | Lee et al. | | 606/192 |
| 6,991,626 B2 * | 1/2006 | Wantink et al. | | 604/524 |
| 7,048,713 B2 * | 5/2006 | Wang | | 604/96.01 |
| 2002/0082553 A1 * | 6/2002 | Duchamp | | 604/103.06 |
| 2003/0032920 A1 * | 2/2003 | Wantink | | 604/103 |
| 2003/0032921 A1 * | 2/2003 | Duchamp | | 604/103 |
| 2003/0088265 A1 | 5/2003 | Kastenhofer | | |
| 2003/0138582 A1 | 7/2003 | Miller et al. | | |
| 2004/0064130 A1 * | 4/2004 | Carter | | 604/523 |
| 2004/0267197 A1 * | 12/2004 | Blankenship | | 604/103.06 |
| 2005/0070846 A1 * | 3/2005 | Wang | | 604/103 |

FOREIGN PATENT DOCUMENTS

| | | |
|---|---|---|
| EP | 1 103 280 A | 5/2001 |
| WO | WO 89/02763 A | 4/1989 |
| WO | WO 03/037419 A | 5/2003 |

\* cited by examiner

34

CATHETER DISTAL TIP

BACKGROUND OF THE INVENTION

The present invention is related generally to medical devices. More specifically, the present invention is related to catheters. The present invention includes the bonding of incompatible catheter elements to one another and distal tips for catheters, including balloon angioplasty catheters and stent delivery catheters, and methods of making them.

Arterial blockages, which are also called stenoses, are typically caused by the build-up of atherosclerotic plaque on the inside wall of an artery. In fact, several such stenoses may occur contiguously within a single artery. This can result in a partial, or even complete, blockage of the artery. As a result of the danger associated with such a blockage, several methods and procedures have been developed to treat stenoses. One such method is an angioplasty procedure which uses an inflatable balloon to dilate the blocked artery. A typical inflatable angioplasty device, for example, is disclosed in U.S. Pat. No. 4,896,669.

Catheters are frequently used to carry and deploy stent at target sites within vessels. Stents have come into increasing use to prevent the widened vessel regions from narrowing after angioplasty. A stent, typically having a tubular shape, can be put in place in the widened vessel region to hold the vessel walls apart and the lumen open in the event the vessel attempts to narrow again. One class of stents requires that the stent be forcibly outwardly expanded to put the stent into position against the vessel walls. Another class of stents, self-expanding stents, can be delivered to a site in a compressed or constrained configuration and released in the vessel region to be supported. The self-expanding stent then expands in place to a configuration having a wide lumen, typically pressing firmly against the vessel walls where released. The stent is commonly placed at a recently dilated, stenosed vessel region.

Size and construction of a catheter is usually dictated by the purpose for which they are used. Vasculature targets are usually difficult to reach requiring a device which can navigate tortuous conduits of varying diameter. As such, certain characteristics are commonly desired. In general, a catheter should have a maximum radial extent or profile no larger than necessary, in part to enable the catheter to reach further into narrower vessel regions. Desirable features further include, but are not limited to, flexibility, trackability and adequate column strength, accuracy and ease of use, ease of manufacture and materials which cause minimal damage to the vasculature.

Typically, balloon catheters include, among other elements, a shaft, a balloon mounted thereon and a relatively soft distal tip, used to promote tracking and to reduce damage. Different parts or elements of catheters are typically bonded together via thermal bonding or adhesive bonding. It is to these issues that the present application is generally directed, taking into consideration general desired features of catheter design and construction.

All US patents and applications and all other published documents mentioned anywhere in this application are incorporated herein by reference in their entirety.

Without limiting the scope of the invention a brief summary of some of the claimed embodiments of the invention is set forth below. Additional details of the summarized embodiments of the invention and/or additional embodiments of the invention may be found in the Detailed Description of the Invention below.

A brief abstract of the technical disclosure in the specification is provided as well only for the purposes of complying with 37 C.F.R. 1.72. The abstract is not intended to be used for interpreting the scope of the claims.

BRIEF SUMMARY OF THE INVENTION

The present invention is generally directed to catheter tip and catheter shaft designs for balloon catheters, as well as construction of such designs wherein thermally incompatible materials are being used.

In certain embodiments of the invention, the distal tip is mounted around the distal end of an inner shaft. Soft distal tip material, such as Pebax® resins (polyether-block co-polyamide polymers) and nylon has a tendency to soften when introduced into the body due the increase in temperature. The softening of the material increases the friction between the guide wire and the inner wall of the distal tip. The soft material gets "sticky" causing the catheter to get hung up on the guide wire. This impedes guide wire movement through the catheter. Mounting the material around the inner shaft reduces the contact between the tip material and the guide wire.

A further aspect of the invention includes having the tip material butted up to the distal waist of the balloon and over the inner shaft. This provides for a more flexible tip because the inner shaft and the tip material are more flexible than the waist of the balloon. This also allows for a shorter waist, improving flexibility.

A further aspect of the invention is that a small amount of the distal end of the distal tip may overhang the distal end of the inner shaft. This allows for a lower introductory profile and for more robustness when being tracked in the anatomy. The overhang can be between 0-7 mm beyond the distal end of the inner shaft. The optimal design would depend on what properties one is trying to achieve. The shorter the overhang, the better the wire movement, whereas the more the overhang, the better flexibility. The amount of tip overhang may be varied to achieve different performance results.

The invention also contemplates an inner shaft which circumferentially is stepped down at its distal end. This allows the inner shaft to receive the distal tip material without increasing the profile, creating a smoother profile.

The invention also contemplates using the distal tip material as a tie layer to facilitate the bonding of two materials which are ordinarily considered to be incompatible for thermal bonding. The most notable example described herein is the use of a tie layer to facilitate the bonding of the waist of a balloon to an inner shaft, wherein the tie layer also forms a distal tip. The distal end of the inner shaft may also be necked down to minimize the profile. These tie layers may also be used in facilitating bonding of other parts of the catheter where two incompatible materials are being used.

The invention contemplates the above mentioned features alone or in various combinations to achieve desired features of catheter design and construction.

These and other embodiments which characterize the invention are pointed out with particularity in the claims annexed hereto and forming a part hereof. However, for a better understanding of the invention, its advantages and objectives obtained by its use, reference should be made to the drawings which form a further part hereof and the accompanying descriptive matter, in which there is illustrated and described a embodiments of the invention.

BRIEF DESCRIPTION OF THE SEVERAL VIEWS OF THE DRAWING(S)

A detailed description of the invention is hereafter described with specific reference being made to the drawings.

FIG. 1a is a cross-section of FIG. 1 shown along lines 1a-1a.

DETAILED DESCRIPTION OF THE INVENTION

Figure 1:
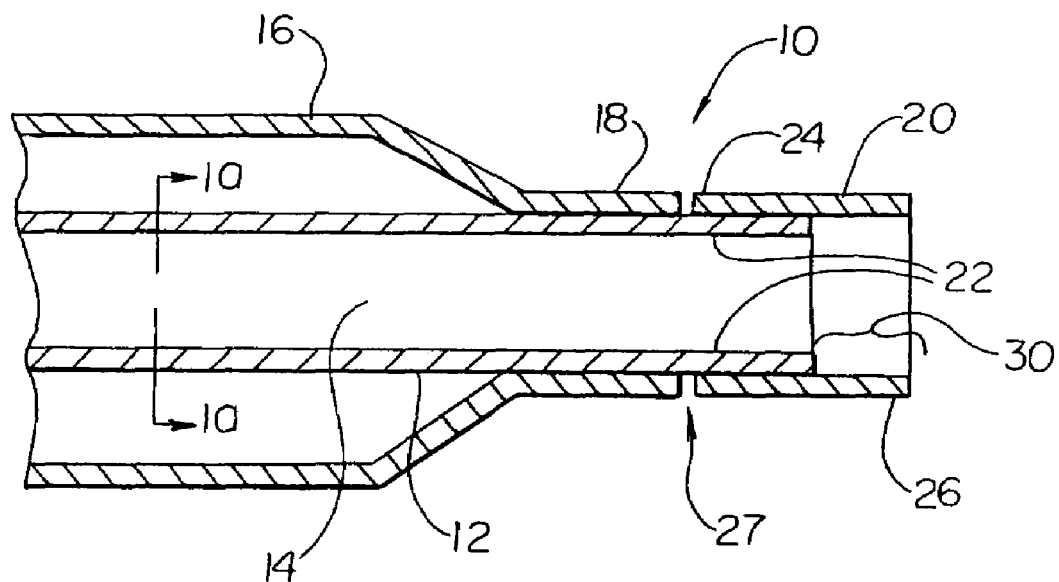
FIG. 1 is a cross-sectional representation of an embodiment of the invention showing the distal end region of a catheter.

While this invention may be embodied in many different forms, there are described in detail herein specific embodiments of the invention. This description is an exemplification of the principles of the invention and is not intended to limit the invention to the particular embodiments illustrated.

For the purposes of this disclosure, like reference numerals in the figures shall refer to like features unless otherwise indicated.

In the description of the inventive catheters of the present application, the figures used only illustrate the distal end of a typical catheter. It should be understood that the tip designs of the present application may be incorporated and used in the construction of any conventional catheter. It also should be understood that the figures are graphic representations of the inventive catheter designs and should not be construed to represent actual dimensions.

As indicated above, the present invention is embodied in a variety of forms. FIG. 1 is a cross-section representation of the invention showing the distal end of a balloon catheter 10. The balloon catheter 10 includes an inner shaft 12 defining a lumen 14. A balloon 16 having a waist portion 18 is secured to the inner shaft 12 by conventional means. A distal tip 20 is further secured to the distal end 22 of the inner shaft 12. The proximal end 24 of the distal tip 20 abuts the waist portion 18 of the balloon 16. A space 27 may be between the proximal end 24 and the distal tip 20 and the waist portion 18 of the balloon 16.

The distal end 26 of the distal tip 20 overhangs the distal end 22 of the inner shaft 12. The margin 30 of overhang may vary. The overhang may be 0-7 mm. In some specific embodiments, the margin 30 is about 0.5 mm to 1.0 mm.

The balloon 16 is secured to the inner shaft 12 through conventional means, including, but not limited to, laser welding and adhering.

The distal tip 20 is secured to the distal end 22 of the inner shaft 12 by laser welding, adhesive bonding or heat shrinking. Adhesive bonding is well known. Examples of thermal bonding can be founding U.S. application Ser. No. 09/654,987.

This overhanging tip design provides, among other benefits, for better guide wire (not shown) movement through the inner shaft 12 lumen 14. Less distal tip material comes in contact with the guide wire than conventional distal tip designs. The present designs also provide more flexibility in the catheter. This, in part, is due to the reduction in length of the distal waist of the balloon.

A comparison was conducted illustrating the improved guide wire movement and flexibility. Results are shown in Tables A and B. The catheter configuration used for sample #'s 1-4 is shown in FIG. 1. The tips of samples 1-2 overhang the inner shaft by 1.0 mm and the tips of samples 3-4 overhang the inner shaft by 0.5 mm. The catheter configuration used in sample #'s 5-14 is the design of the Maverick 2™ sold by Boston Scientific. For samples # 5 and #6, the balloon's distal waist was ground by 25%. These samples otherwise had the identical configuration as the 2.5 mm balloon distal waist group. Sample #'s 7-14 have varying balloon distal waist lengths.

Table A is the spring rate of the tip when tracked around a tight bend. The lower the spring rate the easier it is to navigate the curve. Table B is the peak force (grams) required to track the curve. The lower the force the more flexible the tip is. If you look at Table B, you see that the ground balloons require the least amount of force to track around the curve.

TABLE A

| Description | # | Run 1 | Run 2 | Run 3 | Average |
|---|---|---|---|---|---|
| | | (grams/cm) | | | |
| 1.0 mm Tip overhang | 1 | 84.9 | 79.3 | 80.8 | 81.7 |
| 1.0 mm Tip overhang | 2 | 87.0 | 83.7 | 80.5 | 83.7 |

TABLE A-continued

| | | (grams/cm) | | | |
|---|---|---|---|---|---|
| Description | # | Run 1 | Run 2 | Run 3 | Average |
| 0.5 mm Tip overhang | 3 | 63.2 | 62.4 | 60.2 | 61.9 |
| 0.5 mm Tip overhang | 4 | 56.6 | 57.1 | 63.8 | 59.2 |
| 25% Ground Balloon | 5 | 78.9 | 77.5 | 77.1 | 77.8 |
| 25% Ground Balloon | 6 | 78.4 | 71.3 | 75.8 | 75.2 |
| 2.5 mm Balloon waist | 7 | 108.3 | 98.5 | 95.6 | 100.8 |
| 2.5 mm Balloon waist | 8 | 109.4 | 97.4 | 105.3 | 104.0 |
| 3.5 mm Balloon waist | 9 | 102.5 | 103.4 | 104.8 | 103.6 |
| 3.5 mm Balloon waist | 10 | 102.9 | 95.4 | 93.5 | 97.3 |
| 4.5 mm Balloon waist | 11 | 105.2 | 99.1 | 94.2 | 99.5 |
| 4.5 mm Balloon waist | 12 | 103.1 | 112.7 | 110.1 | 108.6 |
| 2.5 mm Balloon waist | 13 | 86.9 | 74.3 | 78.2 | 79.8 |
| 5.5 mm Balloon waist | 14 | 100.0 | 86.7 | 86.5 | 91.0 |

TABLE B

| | (grams) | | | |
|---|---|---|---|---|
| # | Run 1 | Run 2 | Run 3 | Run 4 |
| 1 | 57.0 | 50.5 | 47.8 | 51.8 |
| 2 | 61.7 | 54.2 | 53.7 | 56.5 |
| 3 | 62.4 | 53.8 | 52.9 | 56.3 |
| 4 | 55.2 | 51.6 | 50.6 | 52.4 |
| 5 | 51.9 | 47.8 | 47.3 | 49.0 |
| 6 | 48.9 | 45.8 | 45.2 | 46.7 |
| 7 | 74.3 | 65.3 | 63.6 | 67.7 |
| 8 | 72.3 | 67.1 | 65.3 | 68.2 |
| 9 | 72.3 | 66.9 | 63.9 | 67.7 |
| 10 | 78.5 | 74.2 | 72.2 | 75.0 |
| 11 | 76.3 | 68.9 | 65.6 | 70.3 |
| 12 | 76.7 | 70.7 | 70.1 | 72.5 |
| 13 | 81.6 | 74.3 | 74.5 | 76.8 |
| 14 | 81.4 | 73.7 | 72.3 | 75.8 |

The amount of tip overhang may be varied to achieve different performance results. With a given peak force to track around a curve, you can adjust your tip length to change your effective spring rate of the tip.

Figure 1A:
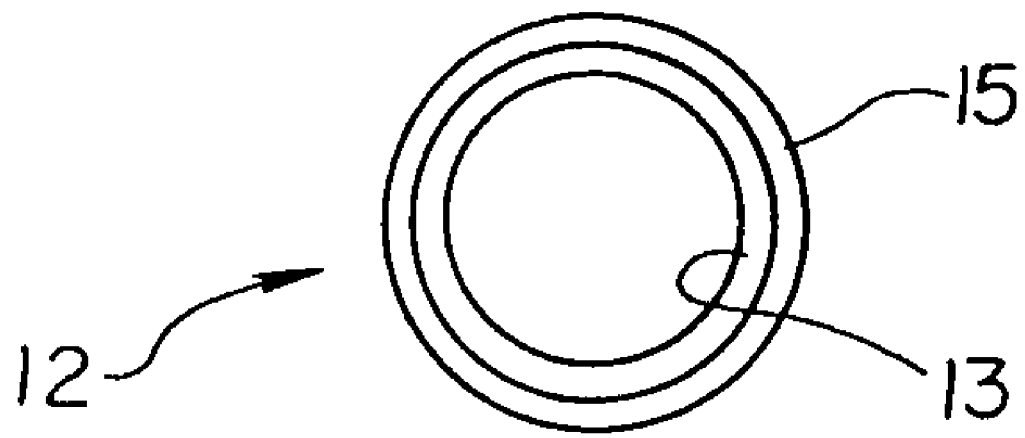

The inner shaft 12 may comprise two or more layers of material, which may be co-extruded to form the shaft 12. FIG. 1a shows a possible cross-section of the inner shaft 12. The inner layer 13 may be formed of a lubricious material, such as, but not limited to, high density polyethylene, while the outer layer 15 may comprise material such as, but not limited to, Pebax™ (polyamide-polyether-polyester block copolymer). The inner shaft 12 may also have a middle layer, such as Plexar® (anhydride modified linear low density polyethylene) between the polyethylene layer and the Pebax™. The middle layer compatibly bonds with both the inner 13 and outer layer 15. It should be understood that the inner shafts of the various embodiments shown and discussed may be multilayered.

Figure 2:
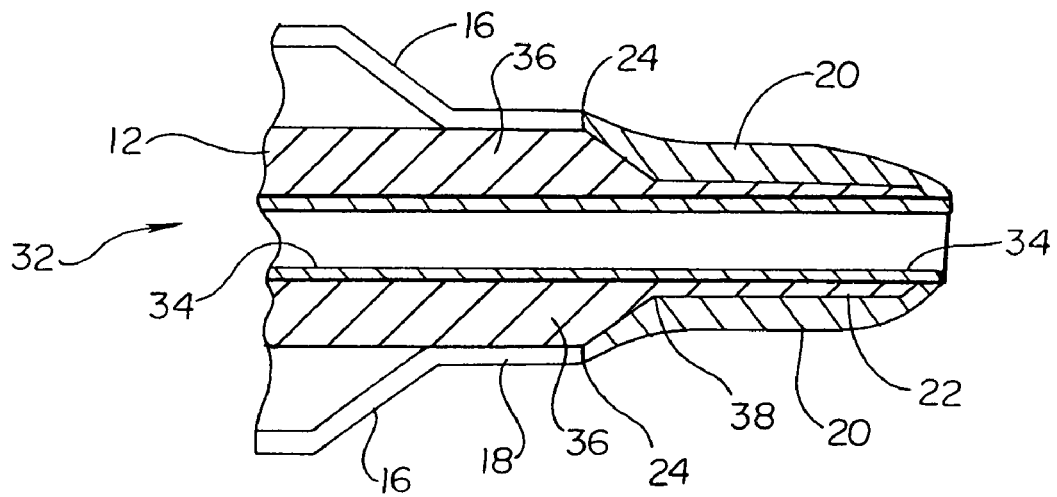
FIG. 2 is a cross-sectional representation of an embodiment of the invention showing the distal end region of a catheter.

A further illustration of the invention is depicted in FIG. 2, which shows a cross-section representation of the distal end of a balloon catheter 32. In this representation, the inner shaft 12 is a multilayer shaft formed from an inner layer 34 and an outer layer 36. The inner layer 34 in one embodiment is a tube of polyethylene. Other materials include nylons, such as Grilamid™ (nylon 12), Pebax™ and Hytrel® (thermoplastic polyester elastomer). The outer layer 36 is extruded, or otherwise applied, onto the inner layer 34 by conventional means. It should be understood, as mentioned above that the layers may be co-extruded. The outer layer 36 in one embodiment is a hard Pebax® material (polyamide-polyether-polyester block copolymer 63D, 66D, 68D, 70D and 72D), or may be Hytrel™ and other Nylon 12's, such as Grilamid™. The inner shaft 12 has a necked-down portion 38, wherein the distal end 22 inner shaft 12 is ground down to receive the softer distal tip 20. The distal tip 20 material in one embodiment is a soft Plexar®, Pebax® (55D-72D) or nylons, such as Grilamid™. In this representation of the invention, the distal tip 20 distally terminates approximately flush with the inner shaft 12, however, it should be understood that, as described above, the distal tip 20 may extend beyond the inner shaft 12. The distal tip material 20 may flow and be drawn out distally during the heating process producing a sloping or narrowing tip, as shown in FIG. 2.

Also, in this representation shown in FIG. 2, the proximal end 24 of the distal tip abuts the waist portion 18 of the balloon 16, which is secured to the outer layer 36 of the inner shaft 12, via conventional means.

Figure 3:
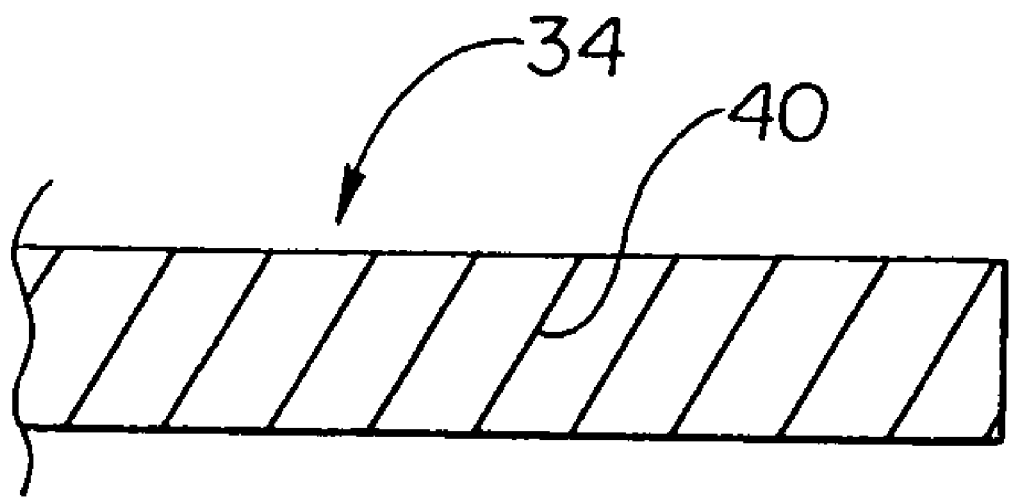
FIG. 3 is a side perspective view of the distal end of an embodiment of the inner shaft.
Figure 4:
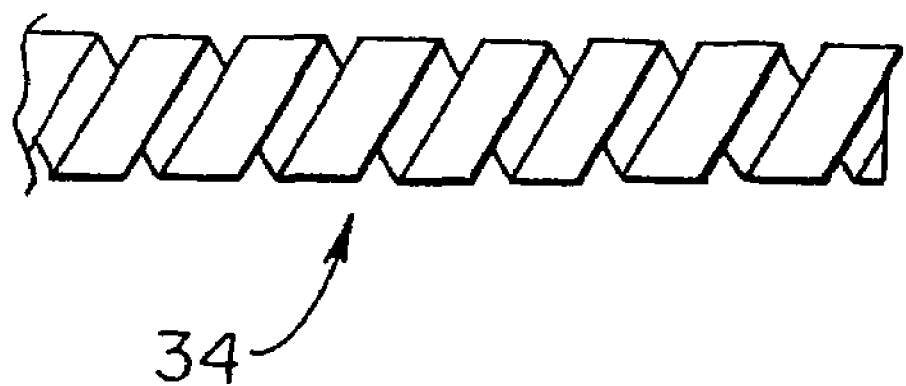
FIG. 4 is a side perspective view of the distal end of an embodiment of the inner shaft.

FIGS. 3-4 show a further aspect of the invention. As shown, the inner layer 34 of the inner shaft 12 may be cut 40 or scored to reduce surface contact with the guide wire and to increase flexibility. The cut may be a spiral cut, as shown in FIG. 3, or several parallel circumferential cuts may be made (not shown). The adjacent ribbon portions may be in contact, as shown in FIG. 3, or they may be separated, as shown in FIG. 4. This cutting or scoring may also be done to the waist portion(s) 18 of the balloon 16, either partially or substantially along the entire waist.

FIGS. 5-17 illustrate further representations of the invention. In addition to the features described above, in these representations, the distal tip 20 further acts as a tie layer between the balloon waist 18 and the inner shaft 12. A tie-layer acts in bonding two materials, typically two incompatible materials, together via laser welding, or other thermal bonding methods. For example, a balloon made of PET (polyethylene terephthalate) and an inner shaft made of Pebax® do not easily, covalently bond to one another. A tube of distal tip material may act as a tie-layer sleeve or a "compatibilizer", wherein the outer layer or surface of tie-layer would be compatible with the balloon material and the inner layer would be compatible with the inner shaft material. In this particular example, a tie-layer sleeve is a two layer sleeve made of EMS (EA20HV1 Grilamid: EA-Nylon 12 (modified) 20-medium viscosity HV1-Adhesion (modified)) and Hytrel® (polyether-ester copolymer) by Du Pont Co. The tie-layer sleeve is coextruded to form a tube with an outer layer made of Hytrel®, which is compatible with PET, and an inner layer made of EMS, which is compatible with Pebax®. The tie layer may also be applied in the form of a liquid by spraying, microdrop, dip or otherwise applying the liquid to the substrate. A powder tie layer, as seen in U.S. application Ser. No. 10/055,743, filed Jan. 23, 2002, is also contemplated. The distal tip layer could also be from a tube with material removed through punched or laser cut holes/slots.

The materials of the layers of the tie layer are dictated by the material of the elements which are to be bonded. The side of the tie layer which faces each element would be compatible therewith. The tie layer need only be one layer if the material of the one layer is compatible with both of the elements which are to be bonded. When two compatible materials are bonded together thermally, they are covalently bonded, as apposed to being mechanically bond or molecularly entangled with one another. Such bonds of the invention have minimal delamination and resist peel. The bonds of the present invention substantially comprise covalent connections between the two materials being bonded. Two incompatible layers which are thermally bonded together do not form covalent bonds substantially over the surface area of the bonded area. Rather, entangled or mechanical bonds are formed, which aren't as strong as covalent bonds.

The bonds created in the present invention allows one to connect a balloon to an inner shaft, wherein the balloon material is incompatible with the outer layer of the inner shaft, an create a balloon catheter which resists peal between the balloon 16 and the inner shaft 12, while the balloon is under pressure in excess of 309 psi.

The following are further representations of the present invention, some utilizing a distal tip sleeve as a tie-layer. Some configurations are repetitive as far as configuration of the examples discussed above. They similarly are cross-sectional representations.

Figure 5:
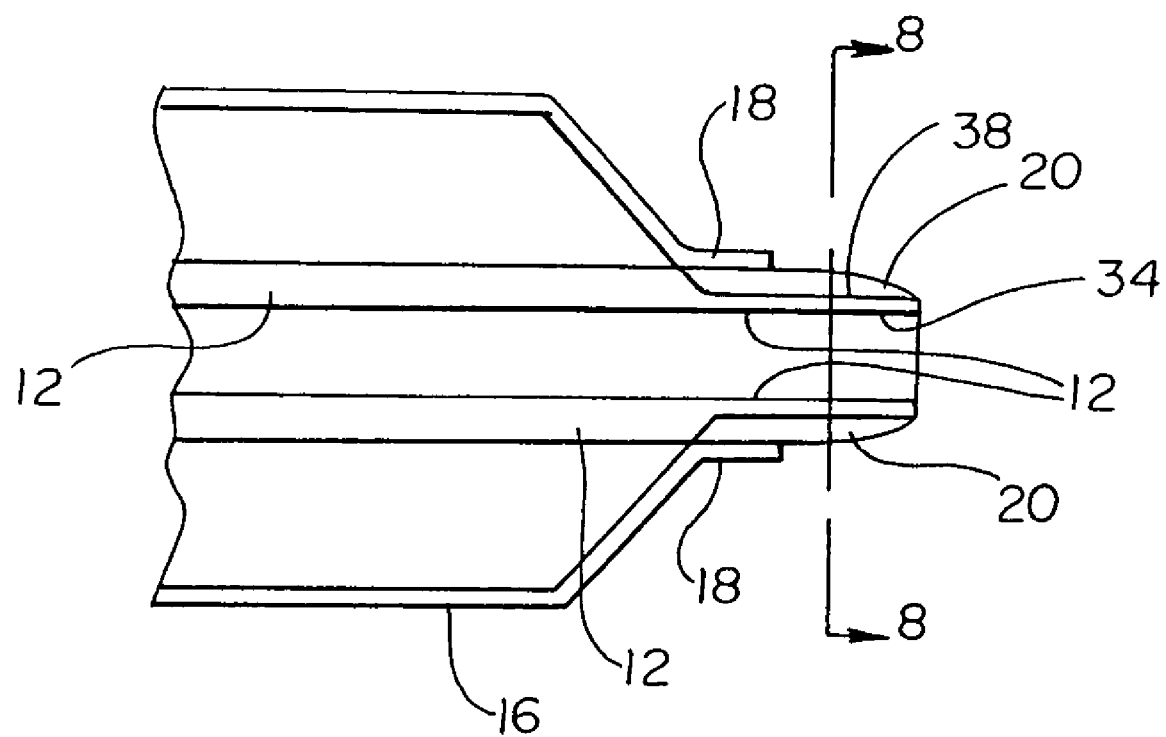
FIG. 5 is a cross-sectional representation of an embodiment of the invention showing the distal end region of a catheter.

In FIG. 5, the distal tip 20 is positioned in the necked-down 38 portion of the inner shaft 12. The waist 18 of the balloon 16 is secured onto the proximal portion of the distal tip 20. As mentioned above, the bonding of the layers may be achieved through conventional means, including, but limited to, laser welding, heat shrinking and adhering.

Figure 8:
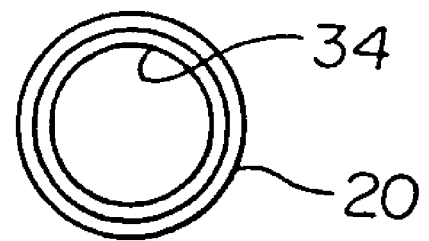
FIG. 8 is a cross-section view of FIG. 5 along lines 8-8.

The distal tip material 20 is pushed or heat shrunk onto the necked-down portion of the inner shaft 12. The waist 18 of the balloon 16 is then held in place over the tip material 20. The layers may be individually adhered or they may be thermally bonded. A tip is thus formed having, as seen in FIG. 8, a thin harder inner layer 34 and a soft outer layer 20. The tip material 20 is used as a tie layer securing the waist portion 18 of a balloon to the inner shaft 12. Such an arrangement improves the integration of the inner shaft, balloon and the soft tip. Due to the necked-down portion of the inner shaft 12, the profile is minimized.

Figure 6:
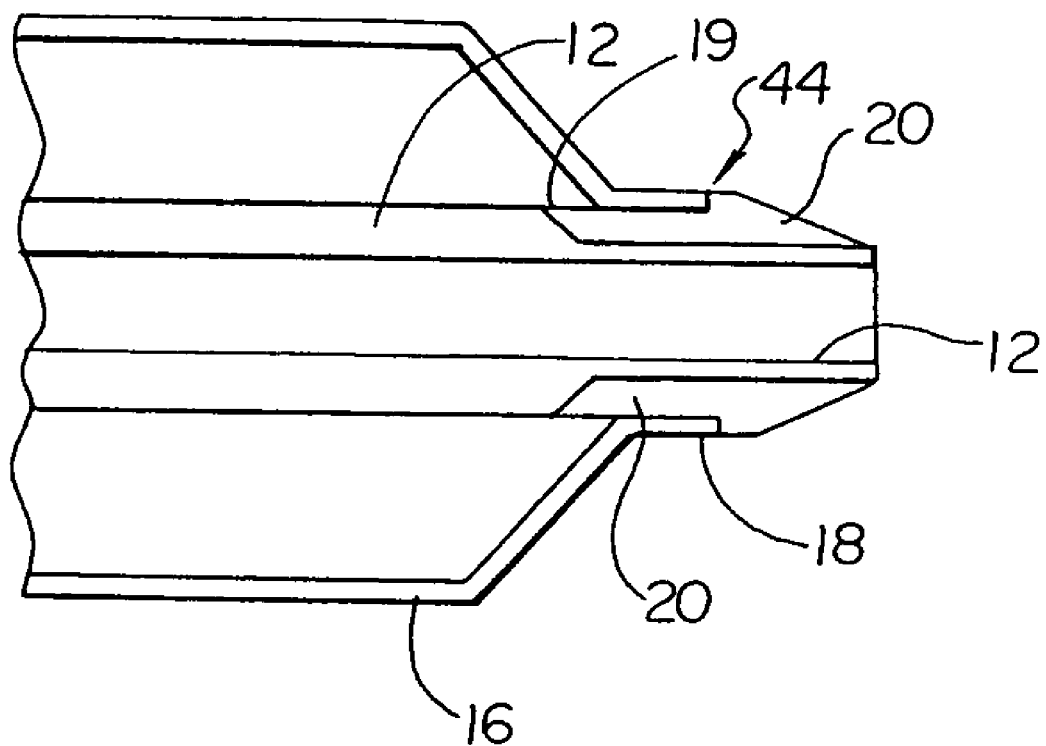
FIG. 6 is a cross-sectional representation of an embodiment of the invention showing the distal end region of a catheter.

FIG. 6's representation of the invention is the same as the one showed in FIG. 5 except that the distal tip 20 material is circumferentially stepped up 44 such that there is a smoother transition from the outer surface of the balloon waist 18 to the outer surface of the distal tip 20. Also, as shown 19, the distal tip material 20 may extend proximally from the balloon waist 18.

Figure 7:
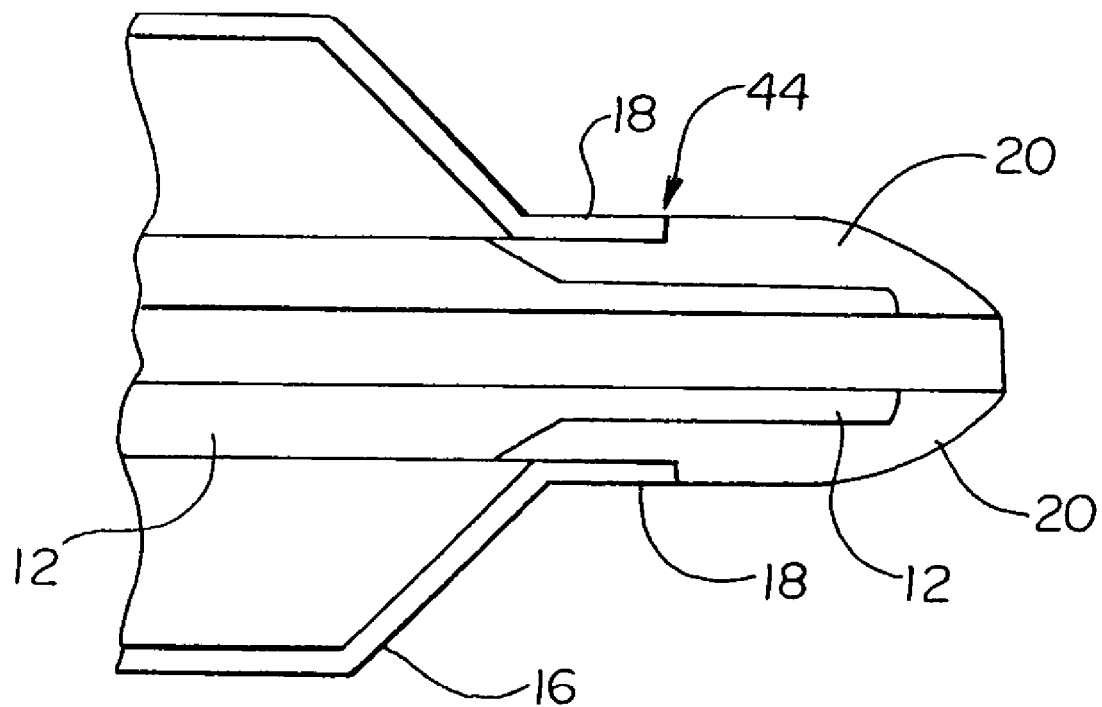
FIG. 7 is a cross-sectional representation of an embodiment of the invention showing the distal end region of a catheter.

FIG. 7's representation of the invention is same as the one showed in FIG. 6 except that the distal tip 20 extends distally beyond the end of the inner shaft 12. This may occur during the heating process, whereby the tip material flows, extending itself distally, as mentioned above, or the tube of tip material may just be longer.

Figure 9:
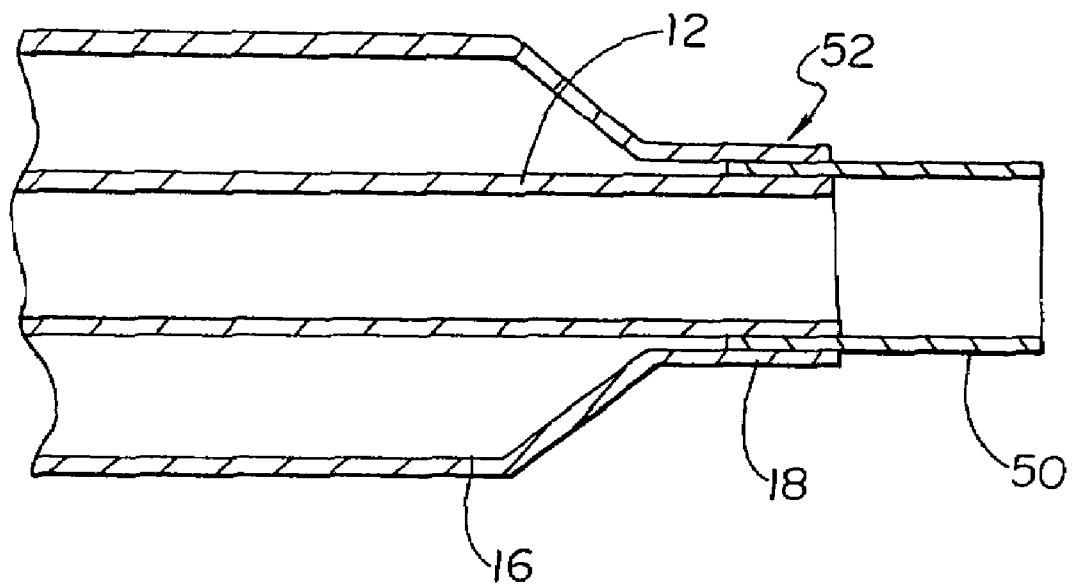
FIG. 9 is a cross-sectional representation of an embodiment of the invention showing the distal end region of a catheter.

FIG. 9 shows the tie-layer 50, which, as mentioned above, may be the tip material 20, about the distal end of the inner shaft 12, extending distally forming the distal tip 50. The waist 18 of the balloon 16 is about the proximal end of the tie-layer 50. The three overlapping layers 52 are thermally bonded. In this embodiment, the ends of the inner shaft 12 and the balloon waist 18 are substantially radially aligned. As with the other embodiments, if the distal tip material 50 is not compatible with the balloon material 16 and the outer surface of the inner shaft 12, a fourth layer may be added in the overlapping region 52 to tie whatever contacting layers which are not compatible.

Figure 10:
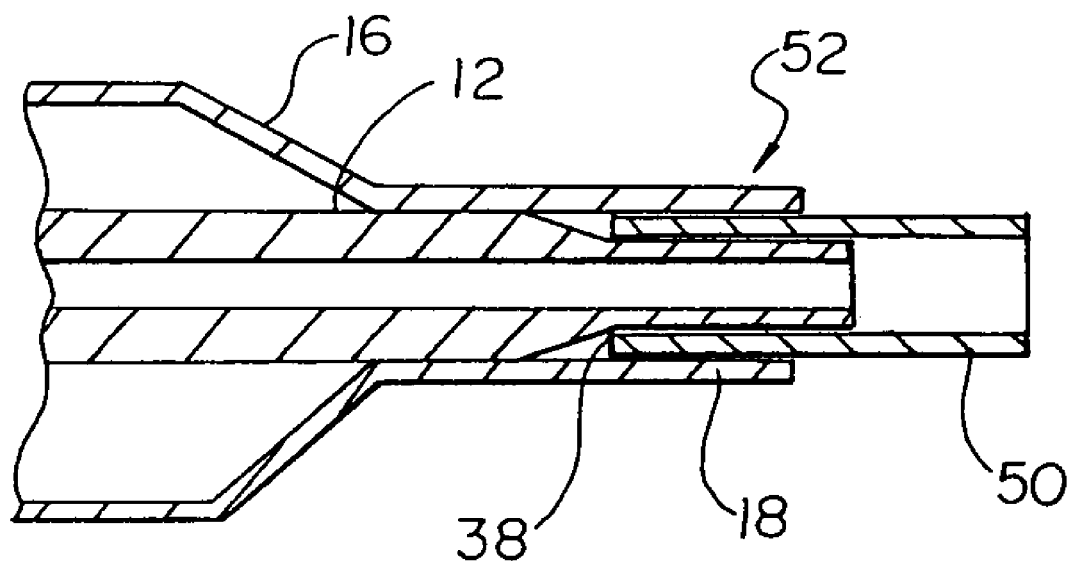
FIG. 10 is a cross-sectional representation of an embodiment of the invention showing the distal end region of a catheter.

FIG. 10 shows a further representation which is the same as shown in FIG. 9, except that in the region of the three overlapping layers 52, the inner shaft 12 is necked down, as described above. As can be seen, the tie layer 50 overhangs the inner shaft 12. The waist 18 may also extend proximately from the necked down portion 38 of the inner shaft 12, as shown. In this embodiment, the end of the inner shaft 12 may extend further than the balloon waist 18. Such a construction moves a potential focal neck region out of the functional area. Thermal processing of extruded tubes removes orientation, which in turn reduces point of yield strength.

Figure 11:
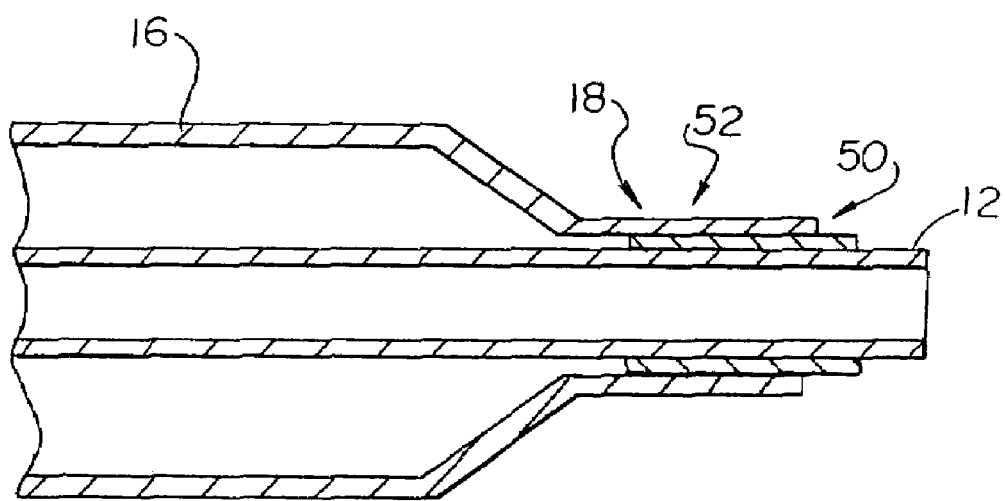
FIG. 11 is a cross-sectional representation of an embodiment of the invention showing the distal end region of a catheter.

FIG. 11 shows an embodiment, wherein the tie layer's 50 distal end terminates prior to the distal end of the inner shaft 12 and balloon waist 18 ends at or prior to the distal end of the tie layer 50.

Figure 12:
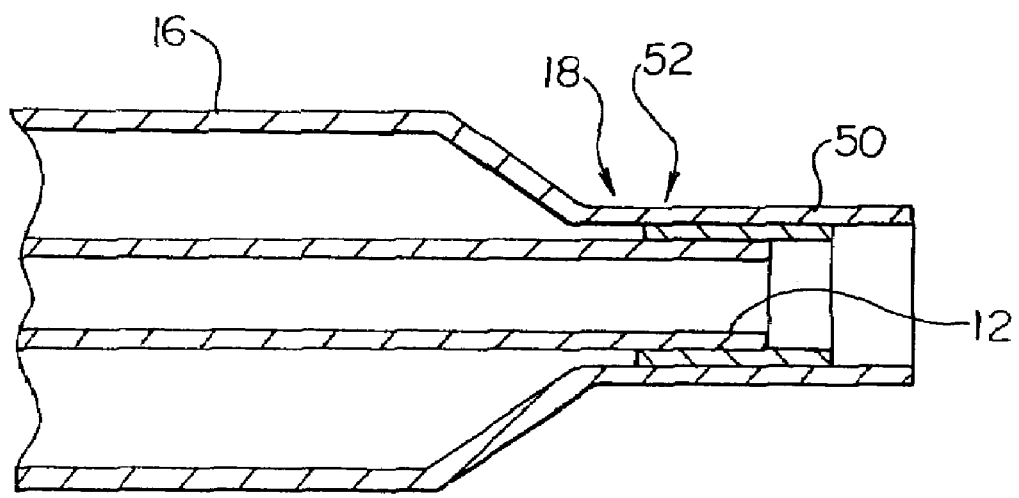
FIG. 12 is a cross-sectional representation of an embodiment of the invention showing the distal end region of a catheter.

FIG. 12 shows an embodiment, wherein the inner shaft 12 terminates at, or prior to, the distal end of the tie layer 50 and wherein the balloon waist 18 extends beyond the distal end of the tie layer 50.

Figure 13:
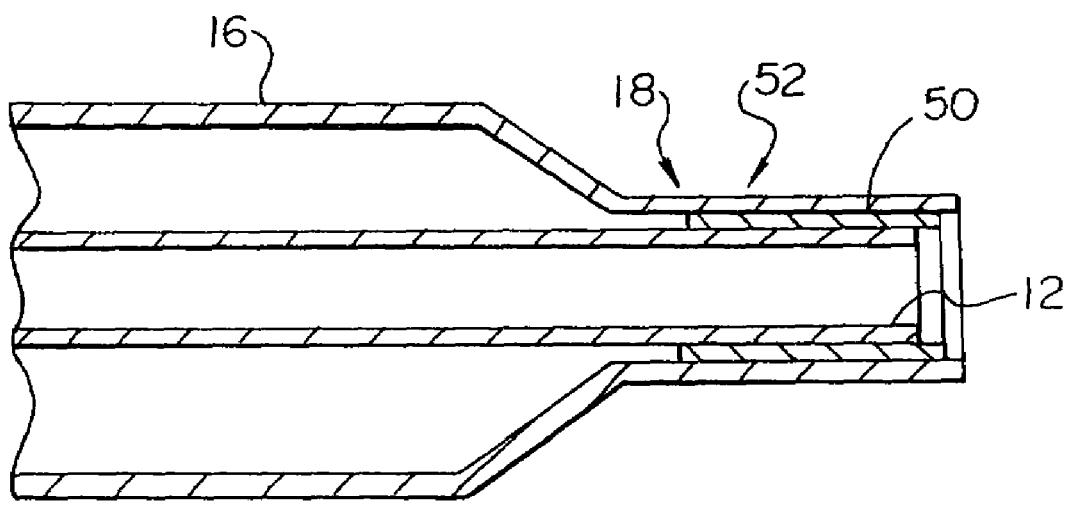
FIG. 13 is a cross-sectional representation of an embodiment of the invention showing the distal end region of a catheter.

FIG. 13 shows an embodiment, wherein the tie layer 50 extends proximally from the proximal end of the balloon waist 18. Also, the inner shaft 12 terminates at or prior to the distal end of the tie layer 50 and the tie layer 50 terminates at or prior to the distal end of the balloon waist 18.

Figure 14:
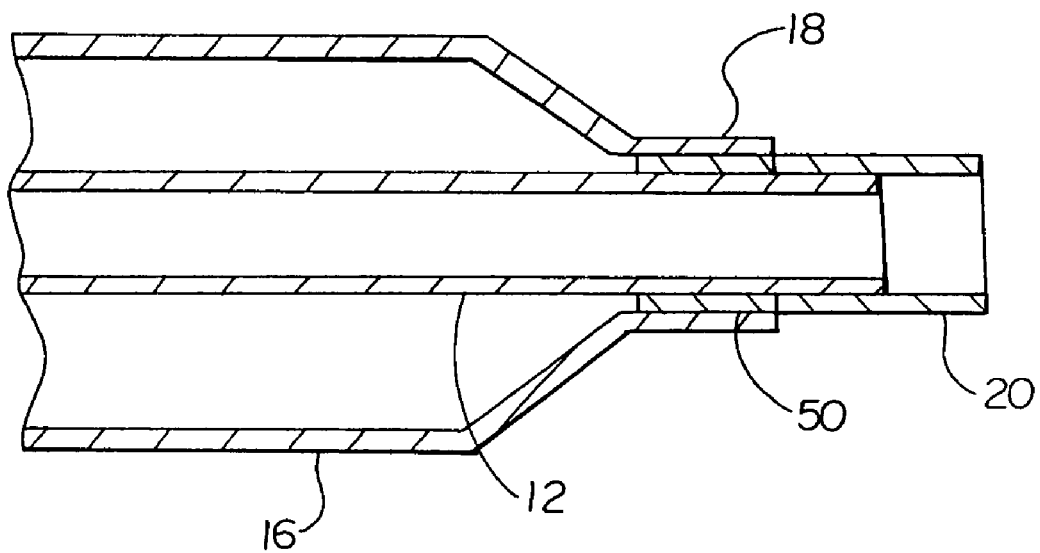
FIG. 14 is a cross-sectional representation of an embodiment of the invention showing the distal end region of a catheter.

FIG. 14 shows an embodiment, wherein the balloon waist 18 is bonded to the inner shaft 12 via a tie layer 50. Abutting the distal end of the tie layer 50 is a distal tip 20, which may be of a material which is different than the tie layer 50 material, wherein the distal tip 20 is about the inner shaft 12 and extends distally beyond the distal end of the inner shaft 12. It should be understood that the distal tip layer 20 may be thicker to provide a flush transition from the balloon waist 18 and further it may thermal drawn out to provide a sloping and narrowing tip.

Figure 15:
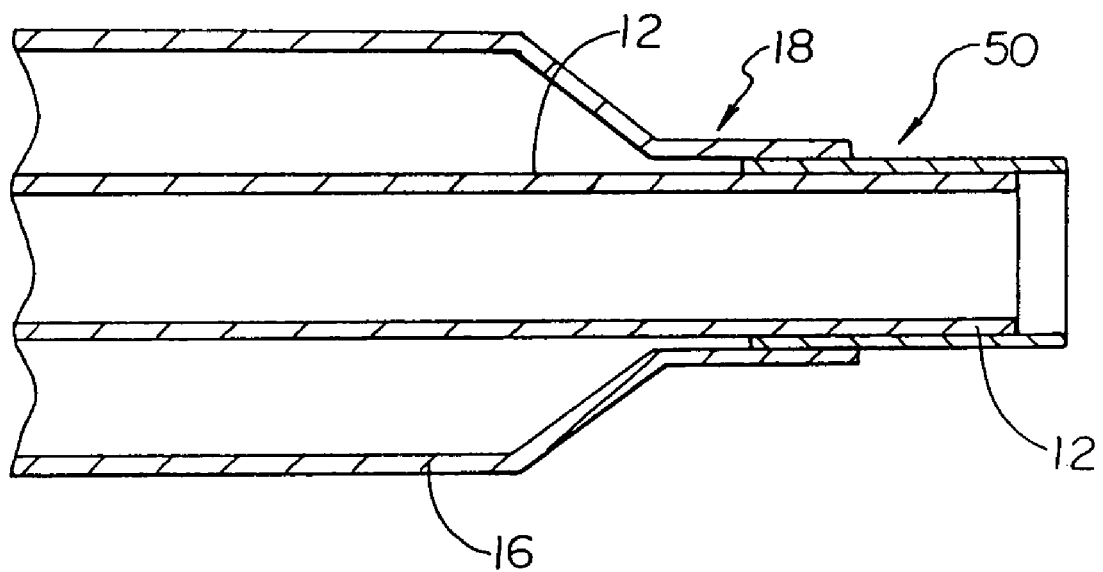
FIG. 15 is a cross-sectional representation of an embodiment of the invention showing the distal end region of a catheter.

FIG. 15 shows the balloon catheter of FIG. 9, except that the inner shaft 12 extends beyond the waist 18 of the balloon 16. As can be seen, the tie layer 50 extends beyond the distal end of the inner shaft 12.

Figure 16:
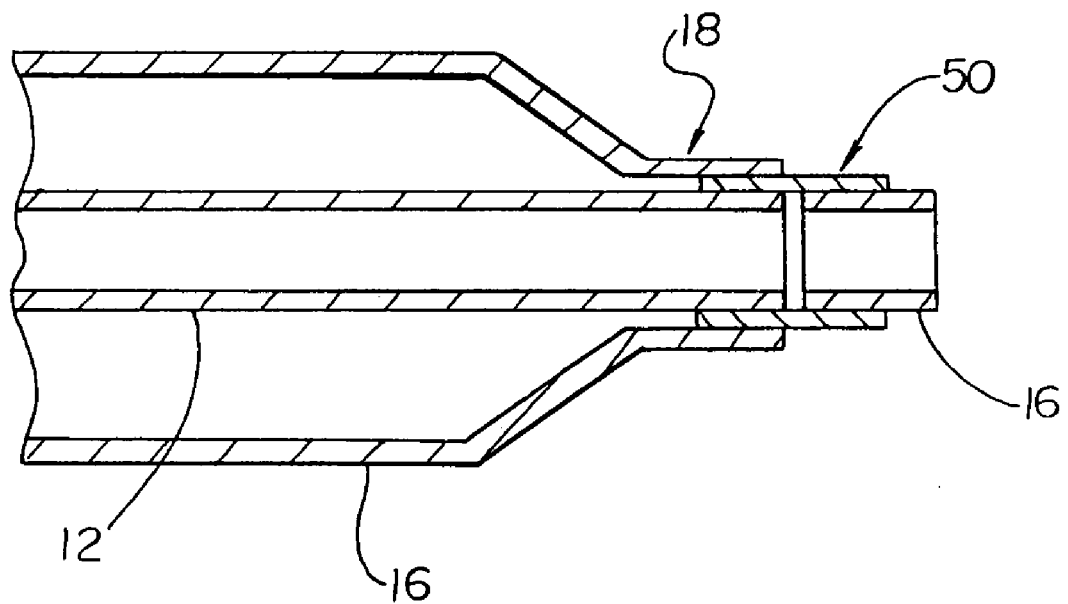
FIG. 16 is a cross-sectional representation of an embodiment of the invention showing the distal end region of a catheter.

FIG. 16 shows an embodiment, wherein a separate distal tip 66 abuts the distal end of the inner shaft 12. The tie layer 50 facilitates the connection between the inner shaft 12 and the distal tip 6 as well as the bonding of the waist 18 to the inner shaft 12. As can be seen in the figure, there may be a small gap between the distal end of the inner shaft 12 and the proximal end of the distal tip 16.

Figure 17:
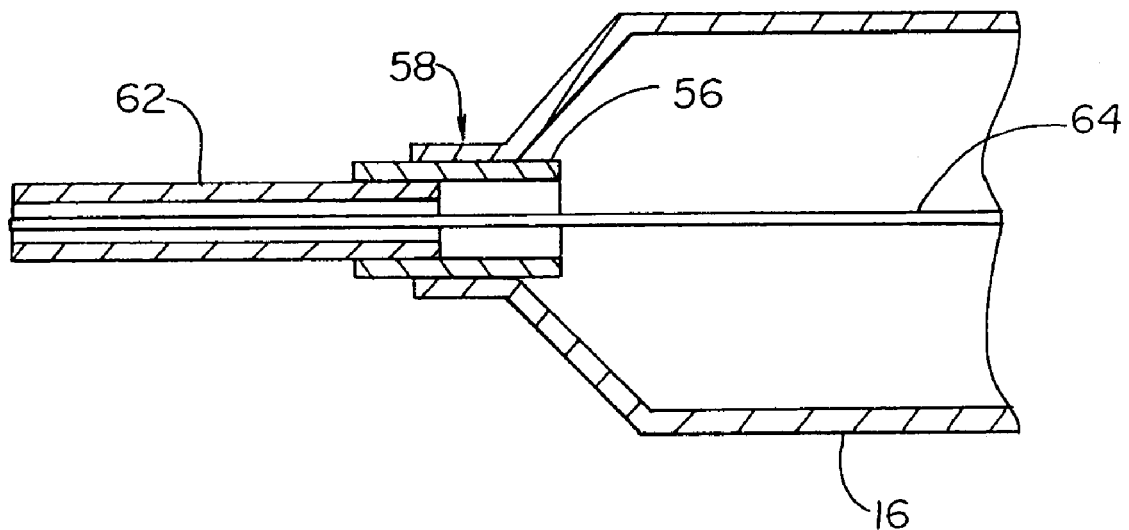
FIG. 17 is a cross-sectional representation of an embodiment of the invention showing the bonding of a proximal balloon waist.

FIG. 17 illustrates a further use of the tie layer 56. In this representation, the tie layer 56 is facilitating the bond between the proximal waist 58 of the balloon 16 to a distal outer shaft 62. In this particular figure a inner shaft 64.

The application of a compatibilizer sleeve or tie layer is also useful in other applications where two materially incompatible elements or joints are to be securely joined together so as to enable laser welding and advanced bonding technologies. These designs enable numerous materials to be thermally welded irrespective to their compatibility and allow greater flexibility in choosing designs of catheters. Further applications include, but are not limited to, proximal bonds, mid-shaft bonds, manifold bonds, steel blade bonds and port weld bonds on catheters.

It should also be understood that grinding a given percent of the balloon waists to remove mass enhances the performance characteristics of the tip designs in such areas as flexibility, trackability, pushability and profile. Such grinding techniques can be found in U.S. Pat. No. 6,193,738. As mentioned above, the balloon waists may cut or scored.

To repeat those mentioned above or in addition to the ones mentioned above, the distal tip 20/50 material may be made of any suitable soft suitable material including, but not limited to, nylons, such as Grilamid® ELY 2694 (tensile modulus 65,250 psi) produced by EMS-Chemie Holding AG/American Grilon, Inc. of Sumter, S.C., polyamide-polyether-polyester block copolymers, such as Pebax® 7033 (flexural modulus 67,000 psi, hardness 72D, but as low as 40D), polyether-ester copolymers, such as Amitel® by DSM Engineering Plastics, polyether-ester copolymers, such as HYTREL by Du Pont Co., high density polyethylene (HDPE), EMS, a polyamide/Arnitel™ blend, and PE anhydride Plexar™ and mixtures thereof. In one embodiment, the distal tip material has a flexural modulus from about 67,000 to about 29,000 psi and a hardness from about 55D to 70D. A low durometer Nylon/Grilamid™ material may be used.

When the distal tip material is being used as a tie layer, as mentioned above, the tie layer material is dictated by the materials which are to be bonded together. Suitable materials include, but are not limited to, are the ones listed above. Examples of incompatible materials which may use a tie layer for thermal bonding include, but art not limited to, HDPE and Pebax, Arnitel and PET, PET and Pebax, PTFE and Pebax. An example of a tie layer would be a double layer sleeve, wherein one layer is EMS and one layer is Hytrel™ or Arnitel™.

To repeat materials mentioned above or in addition to the ones mentioned above, the inner shaft may be made of any suitable material including, but not limited to, HDPE, polyamide-polyether-polyester block copolymers, such as Pebax® 7233, polyetherether ketone (PEEK), polyether-ester copolymers, and PTFE (polytetrafluoro-ethylene). As mentioned above the inner shaft 12 may be formed of multiple layers, which may be coextruded. An example of a three layer inner shaft would be an inner shaft having a Pebax™ outer layer, a PE inner layer and a Plexar™ middle layer sandwiched between the outer and inner layers.

The balloon body 16 may be made of any suitable balloon material including compliant and non-compliant materials and combinations thereof. Some examples of suitable materials for constructing the balloon body 18 include but are not limited to: low pressure, relatively soft or flexible polymeric materials, such as thermoplastic polymers, thermoplastic elastomers, polyethylene (high density, low density, intermediate density, linear low density), various co-polymers and blends of polyethylene, ionomers, polyesters, polyurethanes, polycarbonates, polyamides, poly-vinyl chloride, acrylonitrile-butadiene-styrene copolymers, polyether-polyester copolymers, and polyetherpolyamide copolymers; copolymer polyolefin material available from E.I. DuPont de Nemours and Co. (Wilmington, Del.), under the trade name Surlyn™; ionomer and a polyether block amide available under the trade name PEBAX™; high pressure polymeric materials, such as thermoplastic polymers and thermoset polymeric materials, poly(ethylene terephthalate) (commonly referred to as PET), polyimide, thermoplastic polyamide, polyamides, polyesters, polycarbonates, polyphenylene sulfides, polypropylene and rigid polyurethane; one or more liquid crystal polymers; and combinations of one or more of any of the above.

It should be understood that the embodiments and methods discuss herein may apply to any vascular system of any size.

The above devices may be constructed using a laser welding process to produce the distal balloon bonds. As an example, a tie layer tube is coextruded, such as an EMS/Hytrel™ tube. The EMS/Hytrel™ tube may then be necked and thereafter cut to length forming the tie layer sleeve. A balloon assembly is then provided and the tie layer sleeve is then positioned. The assembly is then held in place via a heat shrink layer. The assembly is then laser welded to form the finished assembly.

The above disclosure is intended to be illustrative and not exhaustive. This description will suggest many variations and alternatives to one of ordinary skill in this art. All these alternatives and variations are intended to be included within the scope of the claims where the term "comprising" means "including, but not limited to". Those familiar with the art may recognize other equivalents to the specific embodiments described herein which equivalents are also intended to be encompassed by the claims.

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

This completes the description of the alternate embodiments of the invention. Those skilled in the art may recognize other equivalents to the specific embodiment described herein which equivalents are intended to be encompassed by the claims attached hereto.

The invention claimed is:

1. A catheter comprising, a proximal portion, a distal portion, the distal portion terminating at a distal end, a shaft, the shaft having a proximal portion, a distal portion, the distal portion terminating at a distal end, and a conduit there though, and a distal tip layer, the distal tip layer being in the form of a tube and being positioned about the distal portion of the shaft, the distal tip layer having a proximal end and a distal end, wherein the distal end of the distal tip layer extends distally to at least the distal end of the shaft and forms at least a portion of the distal end of the catheter such that the distal tip layer is at least distally coextensive with the shaft, the catheter further comprising a medical balloon, the balloon having a body portion position between a proximal waist and a distal waist, wherein the distal waist is connected to the distal portion of the shaft and is positioned at least adjacent to the proximal end of the distal tip layer and wherein the distal tip layer is circumferentially between the distal waist and the shaft, such that the distal waist is not in contact with the shaft, and wherein the shaft extends distally beyond the distal waist, the distal end of the shaft having a first longitudinal portion having a first diameter, wherein in the first longitudinal portion is radially at least partially within the body portion of the balloon, and a second longitudinal portion having a second diameter, the second longitudinal portion being immediately adjacent to the first longitudinal portion, wherein the first diameter is greater than the second diameter, the second longitudinal portion forming a circumferentially stepped down portion from the first longitudinal portion, wherein the distal tip layer is positioned around and conforms to the circumferentially stepped down portion.

2. The catheter of claim 1, wherein the distal end of the distal tip layer distally extends beyond the distal end of the shaft.

3. The catheter of claim 2, wherein the distal end of the distal tip layer distally extends no more than 1 mm beyond the distal end of the shaft.

4. The catheter of claim 2, wherein the distal end of the distal waist longitudinally abuts a portion of the distal tip layer.

5. The catheter of claim 1, the first longitudinal portion having a first wall thickness and the second longitudinal portion having a second wall thickness, wherein the first wall thickness is greater than the second wall thickness.

6. The catheter of claim 5, wherein the shaft comprises a first layer and a second layer, the second layer being about the first layer, wherein the first layer and the second layer are made out of different materials.

7. The catheter of claim 6, wherein the second layer comprises Pebax and the first layer comprises polyethylene.

8. The catheter of claim 6, wherein the first layer is cut.

9. The catheter of claim 8, the second layer being a tubular layer and the first layer being a tubular layer within the second tubular layer and having a length, wherein the cut is a spiral cut that extends along the length of the first tubular layer.

10. The catheter of claim 9, wherein a spiral space is formed by the spiral cut.

11. The catheter of claim 6, the first layer having a plurality of circumferential cuts.

12. The catheter of claim 5, wherein the distal tip layer is circumferentially stepped to receive the distal waist.

13. The catheter of claim 5, wherein the distal tip layer is a tie layer and wherein the distal waist, the shaft and the tie layer are thermally bonded together.

14. The catheter of claim 13, wherein the distal waist and the shaft are incompatible for thermal bonding.

15. The catheter of claim 1, wherein the distal tip layer extends no more than 7 mm beyond the shaft.

16. The catheter of claim 1, wherein the distal tip layer is a tie layer and wherein the distal waist, the shaft and the tie layer are thermally bonded together.

17. The catheter of claim 16, wherein the distal waist and the shaft are incompatible for thermal bonding.

18. A catheter comprising, a shaft, a first tubular layer circumferentially about the shaft and a second tubular layer circumferentially about the shaft, the shaft and the first and second tubular layers being thermal bonded together, the first tubular layer having an inner side and an outer side and being at least partially circumferentially between the second tubular layer and the shaft, wherein the first tubular layer comprises a layer of EA20HV1 Grilamid: EA-Nylon 12 (modified) 20-medium viscosity HV1-Adhesion (modified) and a layer of thermoplastic polyester elastomer or polyether-ester copolymer and wherein the outer side of the first tubular layer is thermally bonded directly to the second tubular layer and the inner side of the first tubular layer is thermally bonded directly to the shaft and wherein the second tubular layer and the shaft are incompatible for thermal bonding directly to one another, that being that there would be no substantial covalent bonding between the second tubular layer and the shaft after being thermally bonded directly to one another.

19. The catheter of claim 18, the shaft having a proximal portion, a distal portion, the distal portion terminating at a distal end, and a conduit there though, the first tubular layer being positioned about the distal portion of the shaft, the second tubular layer being a medical balloon, the balloon having a body portion positioned between a proximal waist and a distal waist, wherein the distal waist is thermally bonded to the first tubular layer and the first tubular layer is thermally bonded to the shaft.

20. The catheter of claim 19, wherein the outer side of the first tubular layer is compatible for thermal bonding to the distal waist and the inner side of the first tubular layer is compatible for thermal bonding to the shaft.

21. The catheter of claim 19, wherein the shaft extends distally beyond the distal waist and the first tubular layer.

\* \* \* \* \*

UNITED STATES PATENT AND TRADEMARK OFFICE
CERTIFICATE OF CORRECTION

PATENT NO. : 7,575,568 B2  Page 1 of 1
APPLICATION NO. : 10/732983
DATED : August 18, 2009
INVENTOR(S) : Holman et al.

It is certified that error appears in the above-identified patent and that said Letters Patent is hereby corrected as shown below:

On the cover page,

Item [*] Notice: Subject to any disclaimer, the term of this patent is extended or adjusted under 35 USC 154(b) by 325 days Delete the phrase "by 325 days" and insert -- by 485 days --

Signed and Sealed this

Thirteenth Day of April, 2010

David J. Kappos
*Director of the United States Patent and Trademark Office*